(12) United States Patent
Trowell

(10) Patent No.: US 8,731,754 B2
(45) Date of Patent: May 20, 2014

(54) CONTROLLER AND CONTROL METHOD FOR A MOTORISED VEHICLE

(75) Inventor: Matthew John Trowell, Christchurch (GB)

(73) Assignee: Penny & Giles Controls Limited, Dorset (GB)

( * ) Notice: Subject to any disclaimer, the term of this patent is extended or adjusted under 35 U.S.C. 154(b) by 0 days.

(21) Appl. No.: 13/253,733

(22) Filed: Oct. 5, 2011

(65) Prior Publication Data

US 2012/0265384 A1    Oct. 18, 2012

(30) Foreign Application Priority Data

Oct. 11, 2010   (GB) .................................. 1017066.0

(51) Int. Cl.
*B60L 11/00*   (2006.01)
*B62D 39/00*   (2006.01)

(52) U.S. Cl.
USPC .................................. 701/22; 180/907; 280/3

(58) Field of Classification Search
USPC .......... 701/22, 41, 42, 72; 180/6.5, 65.1, 907; 280/3
See application file for complete search history.

(56) References Cited

U.S. PATENT DOCUMENTS

| | | | |
|---|---|---|---|
| 5,033,000 A | 7/1991 | Littlejohn et al. | |
| 5,307,888 A | 5/1994 | Urvoy | |
| 7,138,772 B2 * | 11/2006 | Noro et al. | 318/400.01 |
| 2002/0011361 A1 * | 1/2002 | Richey et al. | 180/6.5 |
| 2005/0085962 A1 * | 4/2005 | Palmer et al. | 701/22 |
| 2005/0087375 A1 * | 4/2005 | Steele et al. | 180/65.1 |
| 2010/0007299 A1 | 1/2010 | Davis et al. | |
| 2011/0239277 A1 * | 9/2011 | Fertell et al. | 726/4 |

FOREIGN PATENT DOCUMENTS

| | | | |
|---|---|---|---|
| GB | 2469654 A | | 10/2010 |
| JP | 63195033 A | | 8/1988 |
| JP | 2660992 | * | 10/1997 |
| JP | 2001-104396 A | * | 4/2001 |
| JP | 2004229716 A | | 8/2004 |
| WO | 02066281 A3 | | 8/2002 |
| WO | 2005039473 A2 | | 5/2005 |

OTHER PUBLICATIONS

JP2001-104396 A: Machine Translation.*
JP2660992: Machine Translation.*
Search Report under Section 17(5) from corresponding Application No. GB1017066.0, mailed Feb. 14, 2011, 5 pgs.
Curtis enAble® 40 Manual, Rev. D; Aug. 2008; 33 pgs.
DX2-REM550/REM551 Installation Manual; GBK60348: Issue 1—Mar. 2008; 34 pgs.

* cited by examiner

*Primary Examiner* — Fadey Jabr
*Assistant Examiner* — Aaron L Troost
(74) *Attorney, Agent, or Firm* — James F. Hann; Haynes Beffel & Wolfeld LLP

(57) ABSTRACT

A controller for a motorised vehicle is provided which is arranged to receive control signals from a user input device and the controller is configured to control a motor arrangement of the motorised vehicle in dependence on the control signals. The controller comprises an acceleration control unit configured to determine a centripetal force factor corresponding to a centripetal force which is currently acting on said motorised vehicle as a result of the control signals and is configured to calculate an acceleration limit for the motorised vehicle in dependence on the centripetal force factor. The acceleration control unit is configured to apply the acceleration limit by modifying a response of the controller to the control signals, such that the motorised vehicle does not exceed the acceleration limit.

17 Claims, 8 Drawing Sheets

CONTROLLER AND CONTROL METHOD FOR A MOTORISED VEHICLE

BACKGROUND OF THE INVENTION

1. Field of the Invention

The present invention relates to a controller and a control method for a motorised vehicle for example an electric wheelchair, wherein the controller receives control signals from a user input device.

2. Description of the Prior Art

Conventional electric wheelchairs have drive wheels which are driven independently by a motor arrangement. Whilst the motor arrangement used to drive the wheels may comprise a single motor with independent couplings between the motor and the wheels to effect independent drive of those wheels, more commonly each driven wheel is driven by an independent motor. Controlling the speed and direction of each driven wheel allows the user to manoeuvre the wheelchair.

A typical input control interface for an electric wheelchair provides a joystick having two control axes, one to control the forward/reverse speed and one to the control the turn rate (or spin). Although such control interfaces ostensibly provide the user with free control over the wheelchair's speed and spin, it is in fact common to impose certain limits on the combinations of speed and spin which the user can request. This is done essentially for safety reasons, because for example a maximum spin request (with a left wheel and a right wheel being driven in opposite directions) might be safely requested when the wheelchair is stationary (to thus pivot on the spot), but such a sharp turn could be dangerous if requested when the wheelchair is already travelling with a substantial linear speed. In a worst case scenario this could cause the wheelchair to topple over.

It is therefore known to impose "gate shaping" on the control interface, which typically allows a greater degree of spin to be requested in combination with lower linear speeds, whilst limiting more restrictively the spin that may be requested in combination with high linear speeds. Such gate shaping is typically implemented by means of an algorithm which transforms signals from the user's control interface into signals which control the motor arrangement of the wheelchair.

Even without entering a regime where the wheelchair is liable to tip over, management of the speed and spin of the wheelchair is still necessary because of the effect that certain combinations of speed and spin can have on the fraction of each wheel during a turn. A loss of traction of one wheel can have undesirable consequences for the handling of the wheelchair when making a turn. One reason why traction may be lost is the centripetal force acting on the wheelchair during a turn, which will tend to lift the inside wheel thus reducing its traction. This problem is worse with front wheel drive wheelchairs since the inside wheel is the high torque wheel and is thus more likely to lose traction. If a significant degree of traction is lost on the inside wheel, then the wheelchair may be liable to spin out of control into the turn. Even without such drastic lost of control, even a smaller loss of traction may cause handling difficulties for the user of the wheelchair. In general a loss of traction of either driving wheel would ideally always be avoided.

Conventional gate shaping approaches to this problem can certainly prevent the wheelchair from overturning, but nevertheless suffer from problems in the handling characteristics of the wheelchair due to the imposed limits on the relative speed and spin affecting the smooth steering feel of the wheelchair, and have led to the overly severe inhibiting of the spin speed in certain joystick demand regions.

An example set of the parameters that may be predetermined in a contemporary wheelchair controller are given in section 4.1 of the "DX2-REM550/REM551 Installation Manual", March 2008, produced by Dynamic Controls.

Some further background technological information to the present invention can be found in the "enAble40 Powerchair Control System" manual produced by Curtis Instruments, Inc. of New York, USA; in U.S. Pat. Nos. 5,033,000 and 5,307,888; and in US Patent Application Publication 2010/0007299 A1.

It would be desirable to provide an improved technique for controlling motorised vehicles which would alleviate the above-discussed problems.

SUMMARY OF THE INVENTION

Viewed from a first aspect, the present invention provides a controller for a motorised vehicle arranged to receive control signals from a user input device of the motorised vehicle, the controller configured to control a motor arrangement of the motorised vehicle in dependence on said control signals, the controller comprising: an acceleration control unit configured to determine a centripetal force factor corresponding to a centripetal force currently acting on said motorised vehicle as a result of said control signals and configured to calculate an acceleration limit for said motorised vehicle in dependence on said centripetal force factor, wherein said acceleration control unit is configured to apply said acceleration limit by modifying a response of said controller to said control signals, such that said motorised vehicle does not exceed said acceleration limit.

In accordance with the present invention, the controller is provided with an acceleration control unit which is configured to determine a centripetal force factor corresponding to a centripetal force which is acting on the motorised vehicle as a result of the current control signals being received from the user input device. The centripetal force factor may simply be a calculation of the centripetal force itself, or may be a quantity which is dependent on the centripetal force. Based on the centripetal force factor the acceleration control unit is then configured to calculate an acceleration limit for the motorised vehicle. Significantly, this acceleration limit can be determined such that the motorised vehicle will not lose traction with the surface on which it is driving. The acceleration control unit is then configured to modify the response of the controller to the control signals, such that the motorised vehicle does not exceed the acceleration limit. Hence the acceleration control unit provided in the controller continuously monitors the effect of the control signals being received from the user input device and modifies the response of the controller to the control signals being received from the user input device in order to prevent the motorised vehicle from exceeding the acceleration limit. Since the traction which the motorised vehicle has on the surface on which it is driving reduces as the centripetal force acting on the motorised vehicle increases, the traction of the motorised vehicle may be more reliably maintained by monitoring the centripetal force which is liable to act on the motorised vehicle. Then, in order to keep the wheel torque under a limit at which traction would be lost, the acceleration of the motorised vehicle can be controlled to remain below a calculated limit.

In some embodiments said motor arrangement drives at least a left wheel and a right wheel and said control signals comprise a demand speed and a demand spin, wherein said demand speed of said motorised vehicle is given by a mean of a demanded left wheel velocity and a demanded right wheel velocity, wherein said demand spin of said motorised vehicle is given by a mean difference of said demanded left wheel velocity and said demanded right wheel velocity, and wherein said acceleration control unit calculates said centripetal force factor in dependence on a product of said demand speed and said demand spin.

In this arrangement the control signals correspond to a demand speed and a demand spin. The inventor of the present invention realised that the centripetal force factor (corresponding to a centripetal force which would act on the motorised vehicle as a result of an unmodified response to the control signals) is proportional to a product of demand speed and demand spin. Hence, a reliable and easily calculated quantity may be derived by determining this product, on the basis of the received control signals.

In some such embodiments, the acceleration control unit is configured to modify said response of said controller by limiting a rate of change of said demand speed. Given that the acceleration acting on each wheel is dependent on a sum of the rate of change of the demand speed and the rate of change of the demand spin, it would be possible to modify the response of the controller by changing both the rate of change of the demand speed and rate of change of the demand spin. However, it has been found that adjustments to rate of change of the demand spin have a negative impact on the steerability of the motorised vehicle in a manner which is not present for modification to the rate of change of the demand speed. Hence, applying the acceleration limit by limiting a rate of change of the demand speed enables the controller to prevent the motorised vehicle from exceeding the acceleration limit, without adversely affecting its steerability.

In some embodiments said acceleration control unit is configured to limit said rate of change of said demand speed by applying a scaling factor to said rate of change, wherein said scaling factor is determined according to the formula: 1−(TTL*demand speed*demand spin), wherein TTL is a preprogrammed factor. Configuring the acceleration control unit in this manner provides that the effect of the acceleration control unit is easily configurable by the user, such that a range of settings are available, from those where the acceleration control unit barely affects the acceleration of the motorised vehicle, to those where the acceleration control unit strongly influences the acceleration of the motorised vehicle.

In some embodiments the acceleration control unit is configured to apply said acceleration limit only for increasing demand speed. It has been found that a loss of traction is most likely to occur when demand speed is increasing and hence the benefits of the present invention are most applicable in this scenario.

In some embodiments, the demand speed and the demand spin are damped. Hence, the acceleration control unit determines the centripetal force factor on the basis of these damped signals. Damping the demand speed and demand spin provides a smoother response characteristic of the motorised vehicle.

Whilst the controller may be configured to determine the centripetal force factor as a centripetal force, it will be appreciated that a given centripetal force may be converted into a centripetal acceleration by accounting for the mass of the motorised vehicle. Hence, according to some embodiments, said acceleration control unit is configured to determine said centripetal force as a centripetal acceleration of said motorised vehicle.

Whilst there are various ways in which the acceleration control unit could implement a limit on the rate of change of the demand speed, in one embodiment said acceleration control unit is configured to effect said rate of change of said demand speed by applying a sequence of discrete increments to said demand speed.

A sequence of discrete increments provides an easily configurable mechanism for the acceleration control unit to implement a change in demand speed. In one such embodiment said acceleration control unit is configured to apply said acceleration limit by reducing an increment size of said discrete increments. It will be recognised that the acceleration limit could be applied in various ways, but reducing an increment size, for example whilst maintaining a standard time interval at which those discrete increments are applied, provides an easily configurable mechanism for the acceleration control unit to implement.

In some such embodiments, said acceleration control unit is configured to provide a non-zero minimum increment size of said discrete increments. It has been found that if the acceleration control unit is configured to allow the increment size to decrease to zero, that the drive feel of the motorised vehicle is negatively affected, in particular because the motorised vehicle seems unresponsive to a changing input. Hence in this embodiment it is advantageous if the acceleration control unit does not allow the increment size to fully approach zero.

The problems of loss of traction that the present invention addresses are particularly prevalent in front wheel drive vehicles, and in some embodiments the motorised vehicle is a front wheel drive vehicle. In such embodiments, when the acceleration control unit is configured to apply the acceleration limit only for increasing demand speed, the acceleration control unit may be configured to only apply this acceleration limit for increasing demand speed in a forward direction.

Embodiments of the present invention comprise a controller for use in a motorised vehicle taking the form of a wheelchair.

Viewed from the second aspect, the present invention provides a motorised vehicle comprising: a motor arrangement; a user input device configured to issue control signals for the motorised vehicle; and a controller according to the first aspect for controlling the motor arrangement independence on said control signals.

In some embodiments, said motorised vehicle is a wheelchair.

Viewed from a third aspect, the present invention provides a method of controlling a motorised vehicle having a motor arrangement, comprising the steps of: receiving control signals from a user input device of the motorised vehicle and controlling said motor arrangement in dependence on said control signals; determining a centripetal force factor corresponding to a centripetal force which is currently acting on said motorised vehicle as a result of said control signals; calculating an acceleration limit for said motorised vehicle in dependence on said centripetal force factor; and applying said acceleration limit by modifying a response to said control signals, such that said motorised vehicle does not exceed said acceleration limit.

Viewed from a fourth aspect, the present invention provides a computer program product comprising a computer program which when executed on a computing device causes a motorised vehicle having a motor arrangement to be controlled in accordance with the method of the third aspect.

Viewed from a fifth aspect, the present invention provides a controller for a motorised vehicle arranged to receive control signals from a user input device of the motorised vehicle, the controller configured to control a motor arrangement of the motorised vehicle in dependence on said control signals, the controller comprising: an acceleration control means for determining a centripetal force factor corresponding to a centripetal force which is currently acting on said motorised vehicle as a result of said control signals and for calculating an acceleration limit for said motorised vehicle in dependence on said centripetal force factor, said acceleration control means for applying said acceleration limit by modifying a response of said controller to said control signals, such that said motorised vehicle does not exceed said acceleration limit.

The above, and other objects, features and advantages of this invention will be apparent from the following detailed description of illustrative embodiments which is to be read in connection with the accompanying drawings.

DESCRIPTION OF THE PREFERRED EMBODIMENTS

Figure 1:
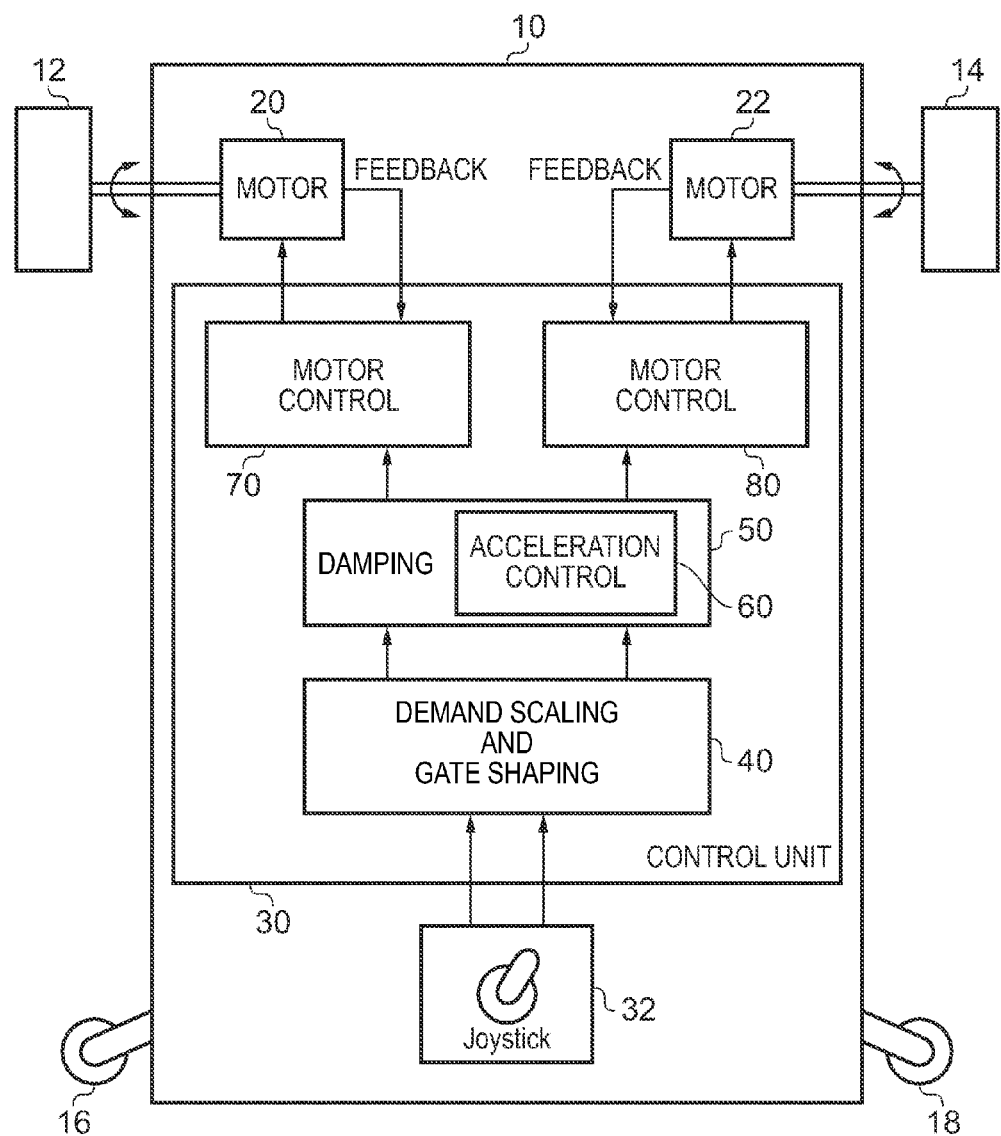
FIG. 1 schematically illustrates a motorised vehicle according to one embodiment.

FIG. 1 is a block diagram of a motorised vehicle in accordance with one embodiment of the present invention. For the purposes of the following discussion, the example where the motorised vehicle is an electric wheelchair will be used. In the example of FIG. 1, the electric wheelchair has a chassis 10 to which two motor driven wheels are connected, namely a left wheel 12 and a right wheel 14. Further, a pair of castors 16, 18 are also provided on the chassis which rotate to follow the direction of the travel of the wheelchair. In the illustrated example, the wheelchair is a front wheel drive wheelchair, so that castors 16, 18 typically follow the direction in which the driven wheels 12, 14 lead (except of course when the wheelchair is in reverse). Each of the two motor driven wheels 12, 14 is driven independently by a motor. In the embodiment illustrated, the left wheel 12 is driven by the motor 20 and the right wheel 14 is driven by the motor 22. To make the electric wheelchair move forwards or backwards, both wheels are driven in the same direction. To make the vehicle turn to the left or right whilst driving, the wheels are driven in the same direction but with different speeds. It is also possible to effect an even tighter turning of the wheelchair, by driving the two wheels 12, 14 in opposite direction which causes the wheelchair to spin on the spot.

As shown in FIG. 1, a control unit 30 is provided on the wheelchair chassis 10 which is coupled to an input control module 32 via which a user of the wheelchair can enter drive commands. In some implementations the control unit may take the form of an embedded processor forming part of the controller of the wheelchair. Whilst the control unit 30 and input module 32 are shown here as separate elements, it will be appreciated that in some embodiments these components may be incorporated into a single housing. As also shown in FIG. 1, the input control module 32 is, in this example, a joystick, which provides an intuitive user-friendly interface. Other input control modules, such as a sip-puff mechanism, are also of course possible. It should be noted that a front wheel drive wheelchair such as that illustrated in the example of FIG. 1 will typically have its joystick mounted near the front of the wheelchair for the convenience of the user. Joystick 32 is positioned in FIG. 1 for schematic clarity alone.

All of the electrical components on the wheelchair receive power from an on-board battery (not illustrated) which is typically a heavy-duty rechargeable battery capable of providing the relatively large currents used to drive the motors 20, 22 during operation of the wheelchair.

The control unit 30 receives control signals from the user input device 32, on the basis of which it generates motor control signals which determine the operation of motors 20, 22. In the illustrated embodiment the joystick 32 is a proportional joystick which provides the control unit 30 with digital control signals indicating a forward ("speed") component and a turn ("spin") component.

In operation, the control unit 30 receives the control signals from the joystick 32, and the control signals are passed to the demand scaling and gate shaping unit 40. This unit modifies the control signals in accordance with predetermined specifications, for example scaling a requested speed by a predetermined factor and limiting the spin which may be requested in combination with a given speed (gate shaping). The modified control signals from the demand scaling and gate shaping unit 40 are passed to damping unit 50 which damps the signals such that a smoother response of the electric wheelchair to changes in control signals from the user results. Damping unit 50 also comprises acceleration control unit 60 which will be described in more detail with reference to the following figures. The damped control signals are then converted into individual motor control signals which are passed to motor control units 70 and 80 which control motors 20 and 22 respectively. The speed control of motors 20 and 22 is performed in accordance with the known IR compensation technique using feedback signals received from each motor.

Figure 2A:
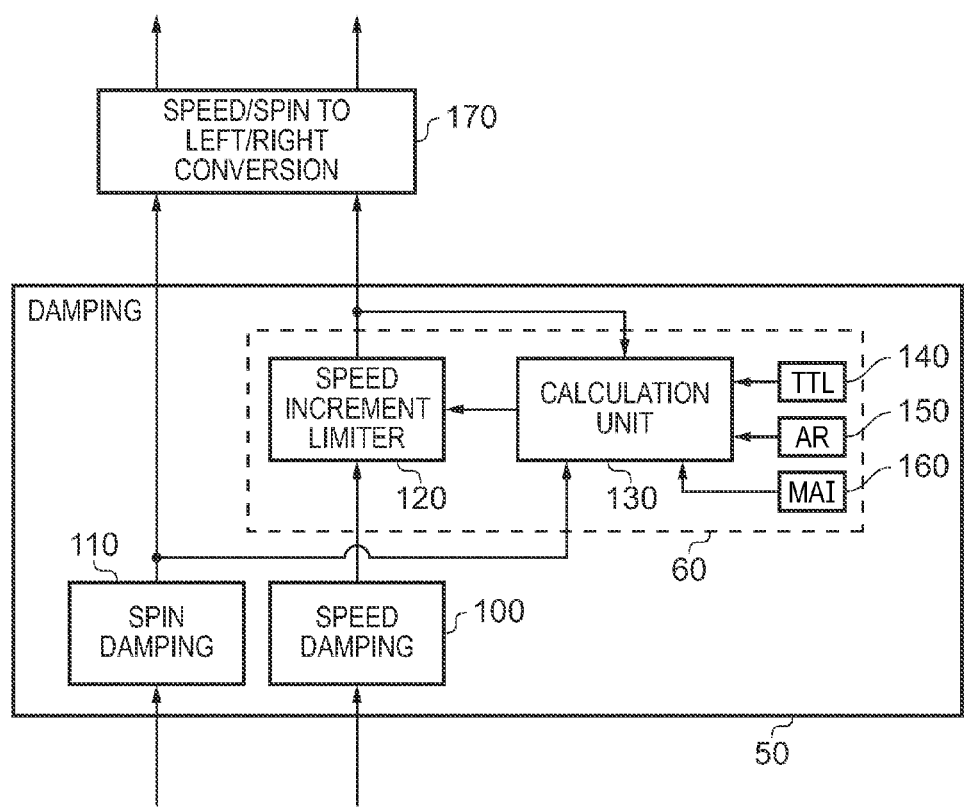
FIGS. 2A and 2B schematically illustrate in more detail two embodiments of the damping and acceleration control circuitry shown in FIG. 1.
Figure 2B:
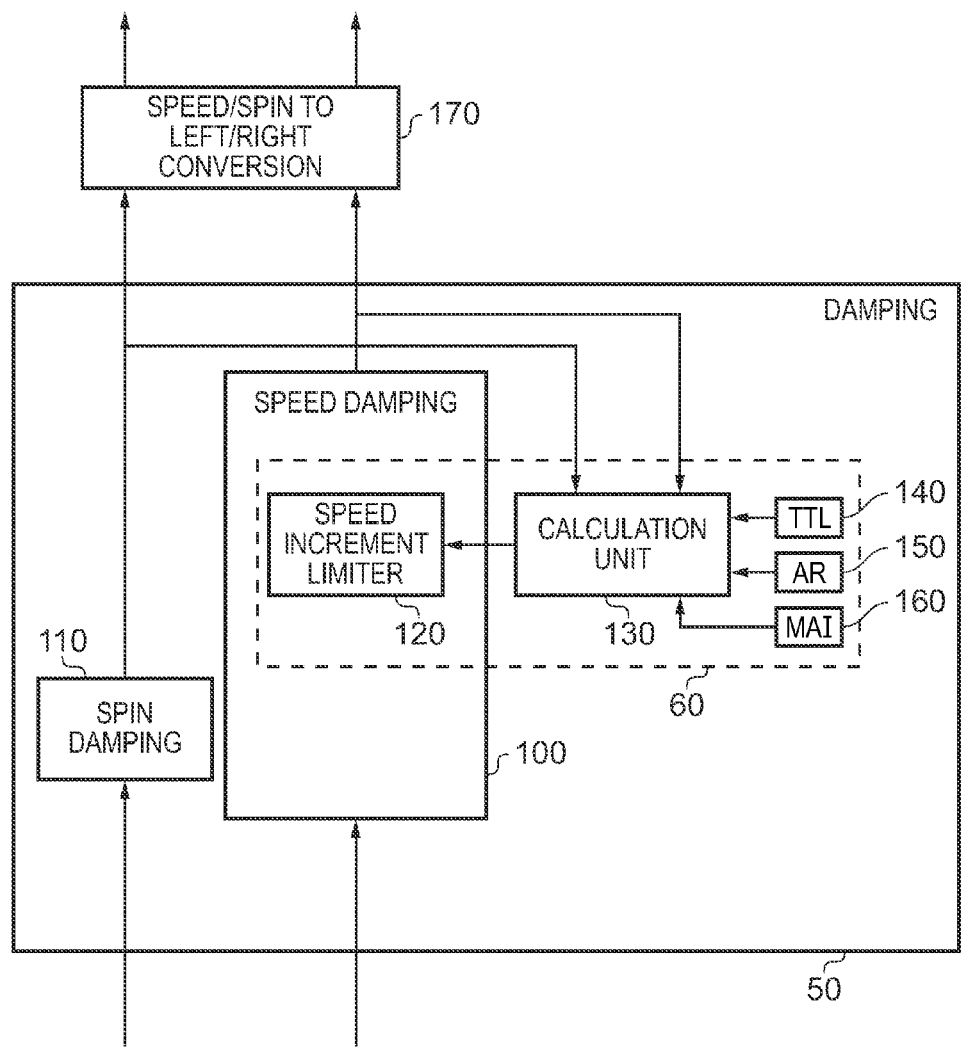

Before discussing the operation of the damping unit 50 and in particular the acceleration control unit 60 in more detail with reference to FIGS. 2A and 2B, it is instructive to first consider some mathematics underlying the motion of the wheelchair.

The speed and spin of the wheelchair may be defined in terms of the velocities (VL, VR) of the left and right wheel 12, 14 as follows:

Equation 1:

$$\text{Speed} = \frac{(VL + VR)}{2}$$

$$\text{Spin} = \frac{(VL - VR)}{2}$$

In terms of these quantities the turn radius of the wheelchair may then be defined as:

Equation 2:

$$\text{TurnRadius} = \frac{L\_axle}{2} \times \frac{\text{Speed}}{\text{Spin}}$$

Where L_axle is the distance between drive wheels 12 and 14. The centripetal acceleration may then be defined as follows:

Equation 3:

$$CentripetalAccel = \frac{Speed^2}{TurnRadius}$$

Combining equations 2 and 3 yields the following, showing that centripetal acceleration is proportional to the product of speed and spin:

Equation 4:

$$CentripetalAccel = \frac{Speed^2}{TurnRadius} = \frac{2}{Laxle} \times Speed \cdot Spin \Rightarrow CentripetalAccel \propto (Speed \cdot Spin)$$

This centripetal acceleration can then be considered in terms of the lifting force acting on the inside wheel of the wheelchair as it turns a corner (with a given TurnRadius) whereby the lifting force is proportional to the centripetal acceleration, which (from Equation 4) gives the relationship between the lifting force and the speed and spin of the wheelchair:

Equation 5:

$$F_{Lift} \propto CentripetalAccel \Rightarrow F_{Lift} = K_1 \cdot Speed \cdot Spin$$

wherein $K_1$ is a proportionality constant which encompasses factors such as the mass of the wheelchair, the height of the centre of mass, the geometry of the wheelchair and the centripetal acceleration constant.

Considering the static friction (f) between the inner wheel and the surface on which the wheelchair is standing in terms of the coefficient of static friction $\mu_s$ and the normal force ($F_N$) acting at the interface between the wheel and the surface, yields the following relationship:

$$f = \mu_S F_n \quad \text{Equation 6:}$$

The normal force $F_N$ is composed of the weight of the wheelchair acting on that wheel, less the lifting force due to the centripetal acceleration:

$$F_n = WheelWeight - F_{Lift} \quad \text{Equation 7:}$$

Now considering the point at which a driven wheel of the wheelchair begins to slip, this can be seen to be equivalent to static friction term f from Equation 6. In other words, the traction between the inner wheel and the surface on which the wheelchair is standing is given by:

Equation 8:

$$Traction = \mu_S F_N \Rightarrow Traction = \mu_S WheelWeight - \mu_S(K_1 \cdot Speed \cdot Spin)$$

The traction limit can then be expressed as an acceleration limit, since the traction force is proportional to the acceleration, introducing a factor $K_2$ to quantify that proportionality:

$$A_{Limit} = K_2\mu_S WheelWeight - K_2\mu_S(K_1 \cdot Speed \cdot Spin) \quad \text{Equation 9:}$$

It should be noted that either Speed or Spin can take a negative value, resulting in an increase in traction on one wheel. However this is correspondingly result in a decrease in traction on the opposite wheel, so when implementing the acceleration limit in practice it is preferable to determine the limit in terms of absolute values of Speed and Spin, namely AbsSpeed and AbsSpin respectively, i.e.:

$$A_{Limit} = K_2\mu_S WheelWeight - K_2\mu_S(K_1 \cdot AbsSpeed \cdot AbsSpin) \quad \text{Equation 10:}$$

Turning now to FIG. 2A, further detail of the damping unit 50 and the acceleration control unit 60 are given. Damping unit 50 receives control signals from demand scaling and gate shaping unit 40 in terms of a requested speed and a requested spin. Speed damping unit 100 and spin damping unit 110 act on these values to produce damped versions which smooth out high frequency variations such that a smoother response of the electric wheelchair to varying control signals generated by joystick 32 results. The damped spin control signal is then passed on to be converted by conversion unit 170 into left and right motor control signals (as is discussed below). The damped speed control signal is passed to speed increment limiter 120 within acceleration control unit 60, which is configured to limit the rate of change of speed in dependence on a signal received from calculation unit 130 which also forms part of the acceleration control unit. The acceleration control unit 60 receives both the damped spin value and the output of speed increment limiter 120. In other words, calculation unit 130 receives the values which are passed by damping unit 50 to the conversion unit 170.

The calculation unit 130 is configured to calculate an acceleration limit in accordance with equation 10 and on that basis to indicate a speed increment limit (i.e. an acceleration limit) to speed increment limiter 120. Calculation unit 130 has three further inputs which are discussed below with reference to FIG. 3. Finally, conversion unit 170 is configured to take speed and spin values and convert these into left and right motor control signals which are passed to motor controls 70 and 80 for driving the left and right motors 20, 22 respectively (i.e. inverting the relationships given in Equation 1 to calculate VL and VR for given values of speed and spin).

FIG. 2B illustrates a minor variation on the arrangement shown in FIG. 2A, in which the speed increment limiter 120 forms part of the speed damping unit 100.

Figure 3:
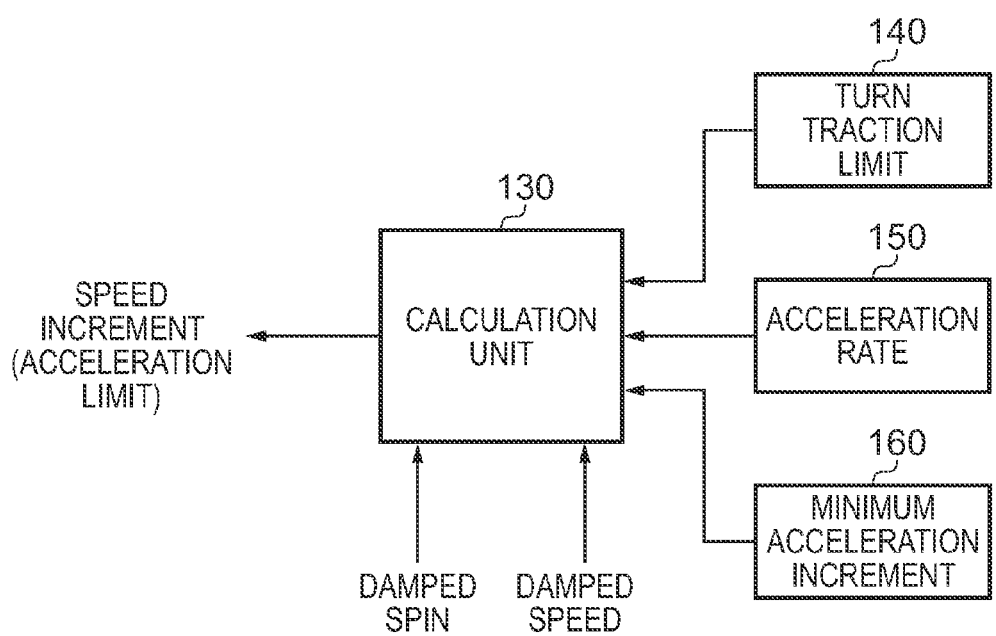
FIG. 3 schematically illustrates in more detail the inputs to the calculation unit shown in FIGS. 2A and 2B.

FIG. 3 schematically illustrates in more detail the inputs to the calculation unit 130. As well as the damped speed and spin values, the calculation unit 130 receives predetermined values which form part of the configuration of the control unit 30, these being represented by turn traction limit 140, acceleration rate 150 and minimum acceleration increment 160. These values are explained in more detail below.

Returning to Equation 9 above, the acceleration limit can be expressed in terms of a scaled maximum acceleration which has been predetermined for the wheelchair:

$$A_{Limit} = A_{Max} A_{Scalar} \quad \text{Equation 11:}$$

wherein:

$$A_{Scalar} = (1 - K_3 \cdot Speed \cdot Spin)$$

$$A_{Max} = K_2\mu_S WheelWeight$$

$$K_3 = \frac{K_1}{WheelWeight}$$

The maximum programmed forward acceleration ($A_{Max}$) is stored as a preprogrammed value (item 150 in FIG. 3) in the control unit. The factor $K_3$ is implemented as a programmable value called the Turn Traction Limit (TTL), which is also stored (item 140 in FIG. 3) in the control unit. For programming convenience, TTL may be implemented as a percentage value between 0 and 100.

It should be noted that in Equation 11 the assumption is made that $A_{Max}$ is the acceleration value at which the wheelchair loses traction for straight-line acceleration (i.e. no centripetal effect).

In order to implement the acceleration limit, the acceleration control unit 60 is configured to limit the increments by which the speed may be adjusted. These adjustments are typically applied at 10 ms intervals, such that applying a limit to the size of the increments puts a limit on the acceleration of the wheelchair.

Figure 4:
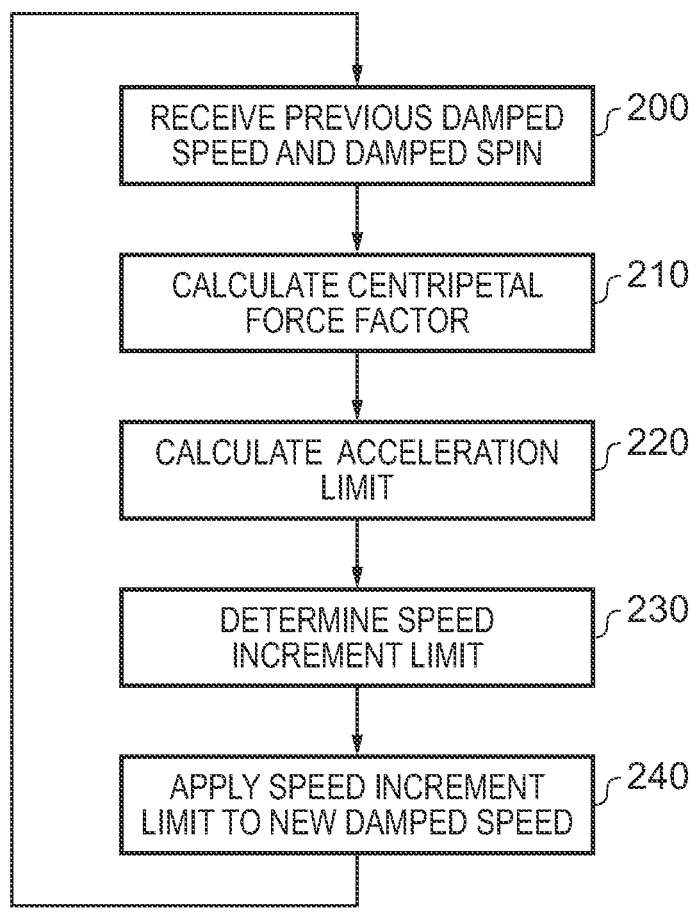
FIG. 4 illustrates a series of steps taken by the acceleration control unit of FIG. 1.

In practice the calculation unit 130 maintains a lower limit ($A_{0\%}$) on the acceleration limit it imposes, since allowing the acceleration increment to fall to zero results in a poor driveability feel for the wheelchair. Hence, the calculation unit 130 also makes reference to a minimum acceleration increment (item 160 in FIG. 3). The acceleration limit calculated by calculation unit 130 and passed as a speed increment limit to speed increment limiter 120 is thus calculated as:

$$A_{Limit} = A_{0\%} + ((A_{Max} - A_{0\%}) \cdot A_{Scalar})$$ Equation 12:

The operation of the acceleration control unit 60 schematically represented in FIGS. 1-3 is now described in terms of a series of steps as schematically set out in FIG. 4. The flow can be considered to begin at step 200 where the acceleration control unit 60 receives values from the previous iteration of damped speed and damped spin. Then at step 210 the calculation unit 130 of the acceleration control unit 60 calculates the centripetal force factor, namely the product of the speed and the spin. This is then converted at step 220 into an acceleration limit for the wheelchair (see equation 9 above) and at step 230 a speed increment limit for the wheelchair is determined. This is applied at step 240 to the new damped speed and the flow returns to step 200.

Figure 5:
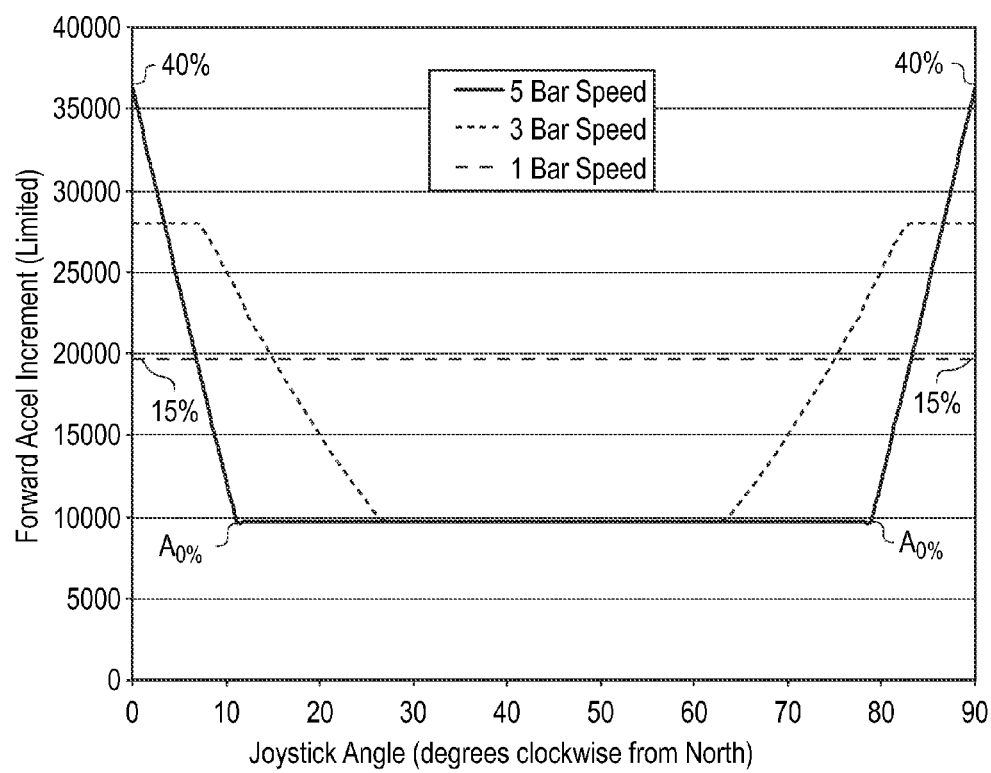
FIG. 5 is a graph showing a simulation of the acceleration increment limit applied by the acceleration control unit with changing joystick angle.

FIG. 5 illustrates a simulation of a first example wheelchair wherein the acceleration increment limit imposed by the acceleration control unit is plotted against the joystick angle. Note that the units of the graph correspond to values used within a fixed point implementation of the acceleration control unit—corresponding percentages are added for ease of reference. The acceleration increment limit is plotted for three different standard speed settings of the wheelchair, namely five bar speed, three bar speed and one bar speed. In this example simulation, the wheelchair has been configured with the following settings:

| | |
|---|---|
| Forward Speed Max | 90% |
| Forward Speed Min | 20% |
| Turn Speed Max | 19% |
| Turn Speed Min | 10% |
| Forward Acceleration Max | 40% |
| Forward Acceleration Min | 15% |
| Turn Traction Limit | 20% |

With these fairly typical settings for the wheelchair, it was found that a turn traction limit of 20% was needed to prevent slippage. It can be seen from FIG. 5 that the pre-programmed maximum forward acceleration (40%) is only available for the 5 bar speed setting when the joystick is fully forwards ("North"). As the joystick is rotated around the gate, the forward acceleration increment rapidly falls, already bottoming out at the minimum acceleration increment ($A_{0\%}$) at a joystick angle of 10 degrees from North. For the 3 bar speed setting, there is a fairly narrow band around North (joystick forwards) where the full forward acceleration available for this speed setting is implemented. Outside of this region, as the angle of the joystick deviates from North, the acceleration increment is reduced until the minimum acceleration increment is reached at approximately 25 degrees from North. For the 1 bar speed setting the pre-programmed minimum acceleration rate (15%) is applied, being sufficiently low that the acceleration control unit does not impose a further limit on the acceleration.

Figure 6:
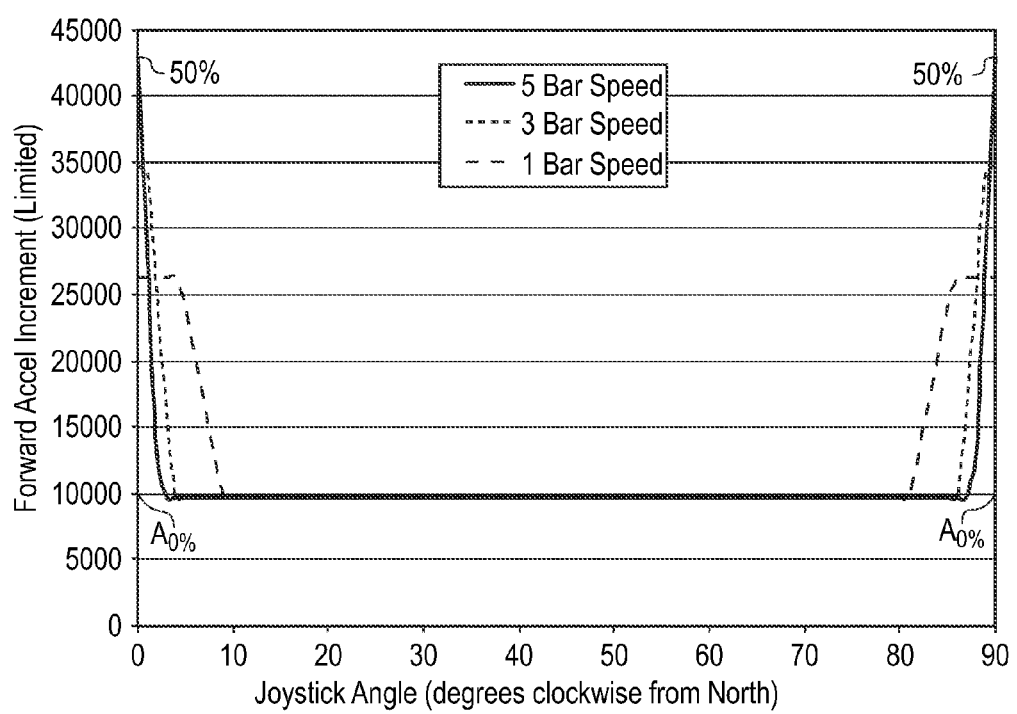
FIG. 6 is a graph showing a simulation of the acceleration increment limit applied by the acceleration control unit with changing joystick angle.

FIG. 6 illustrates a simulation of a second example wheelchair wherein the acceleration increment limit imposed by the acceleration control unit is plotted against the joystick angle. In this example the wheelchair was configured with the following settings:

| | |
|---|---|
| Forward Speed Max | 95% |
| Forward Speed Min | 30% |
| Turn Speed Max | 25% |
| Turn Speed Min | 20% |
| Forward Acceleration Max | 50% |
| Forward Acceleration Min | 25% |
| Turn Traction Limit | 70% |

This second example wheelchair is somewhat heavier than that used for the simulation shown in FIG. 5, and has a relatively high centre of mass. For this wheelchair the programmed acceleration rates and turn speeds are slightly higher than typical programmed values. It was nevertheless found to be possible to stop this wheelchair from losing traction, but a higher turn traction limit of 70% was required to prevent slippage.

As can be seen from FIG. 6, there is only a narrow range of joystick angles over which any variation in the imposed acceleration increment limit exists. For the 5 bar and 3 bar speed settings, the pre-programmed maximum forward acceleration (50%) is only available with the joystick held directly forwards (North), and only a small deviation from this direction causes the acceleration control unit to rapidly impose smaller and smaller allowed increments, with the minimum acceleration increment ($A_{0\%}$) already being reached at joystick angles of less than 5 degrees from North. Even for the 1 bar speed setting, there is only a narrow angular region in which the acceleration increment is unaffected by the acceleration control unit, before being rapidly reduced to the minimum acceleration increment as well.

Figure 7:
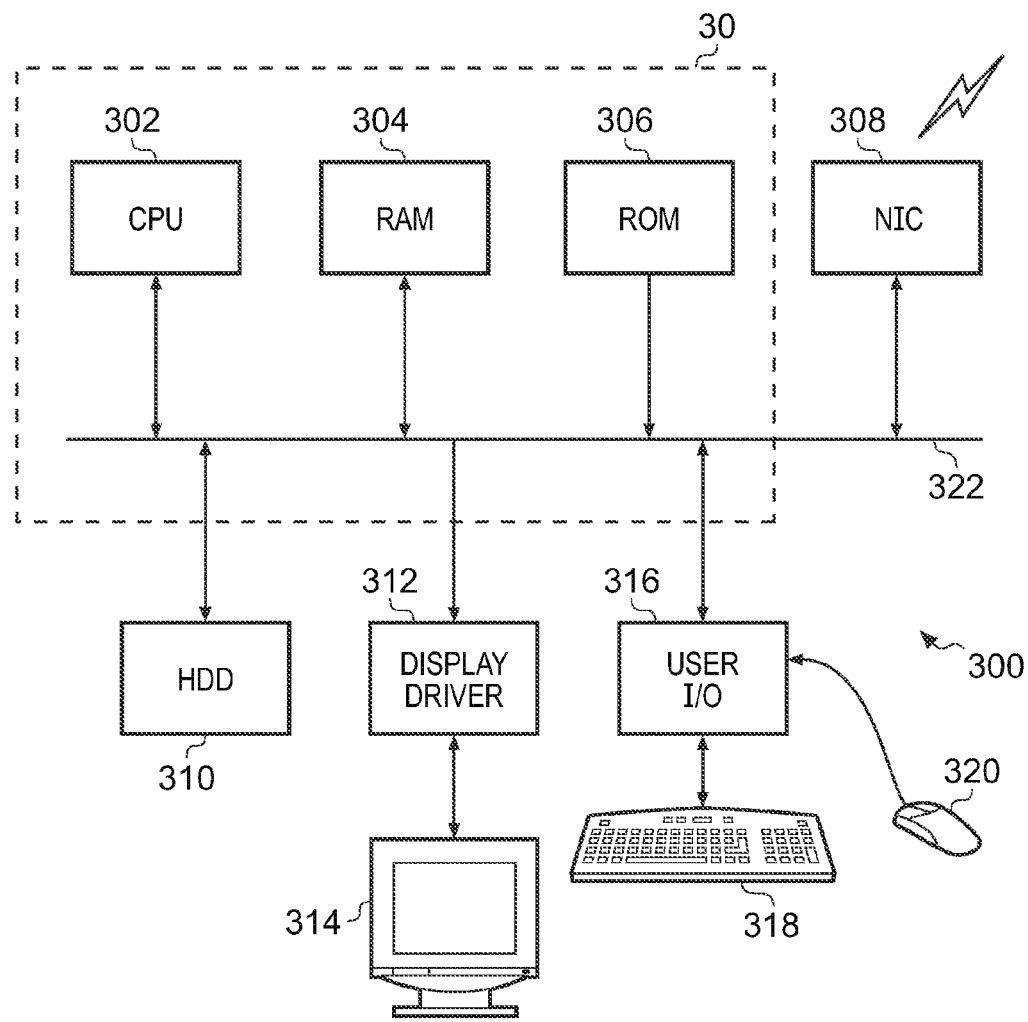
FIG. 7 is a schematic representation of a general purpose computing device which may be used in embodiments of the present invention.

Finally, FIG. 7 schematically illustrates a general purpose computing device 300 of the type that may be used to implement the above described techniques. As mentioned above, in the context of the present invention this could for example be an embedded processor forming part of the control unit of the wheelchair. The general purpose computing device 300 includes a central processing unit 302, a random access memory 304 and a read only memory 306, connected together via bus 322. More fully, the general purpose computing device may be extended to further comprise a network interface card 308, a hard disk drive 310, a display driver 312 and monitor 314 and a user input/output circuit 316 with a keyboard 318 and mouse 320 all connected via the common bus 322. In operation, such as when forming part of the control system of an active wheelchair, the central processing unit 302 will execute computer program instructions that may for example be stored in the random access memory 304 and/or the read only memory 306. These core components of the general purpose computing device are labelled 330 in FIG. 7. The additional components outside the dashed box 30 may additionally be connected, for example when the control system is connected to a diagnostic set-up for pre-programming or for troubleshooting. In such a situation program instructions could be additionally retrieved from the hard disk drive 310 or dynamically downloaded via the network interface card 308. The results of the processing performed may be displayed to a user or an engineer via a connected display driver 312 and monitor 314. User inputs for controlling the operation of the general purpose computing device 300 may be received via a connected user input output circuit 316 from the keyboard 318 or the mouse 320. It will be appreciated that the computer program could be written in a variety of different computer languages. The computer program may be stored locally on a recording medium or dynamically downloaded to the general purpose computing device 300. When operating under control of an appropriate computer program, the general purpose computing device 300 can perform the above described techniques and can be considered to form an apparatus for performing the above described technique. The architecture of the general purpose computing device 300 could vary considerably and FIG. 7 is only one example.

Although a particular embodiment has been described herein, it will be appreciated that the invention is not limited thereto and that many modifications and additions thereto may be made within the scope of the invention. For example, various combinations of the features of the following dependent claims could be made with the features of the independent claims without departing from the scope of the present invention.

Although illustrative embodiments of the invention have been described in detail herein with reference to the accompanying drawings, it is to be understood that the invention is not limited to those precise embodiments, and that various changes and modifications can be effected therein by one skilled in the art without departing from the scope and spirit of the invention as defined by the appended claims.

I claim:

1. A controller for a motorised vehicle of a type having at least two wheels driven by a motor arrangement, the controller comprising:
 a user-actuated input control module comprising a user actuated control element and an output, the input control module capable of providing control signals at said output; and
 a control unit having an input operably coupled to the output of the control module for receipt of the control signals, the control unit comprising:
  an acceleration control unit configured to determine, as a result of said control signals, a centripetal force factor corresponding to a centripetal force currently acting on said motorised vehicle and configured to calculate an acceleration limit for said motorised vehicle in dependence on said centripetal force factor, wherein said acceleration control unit is configured to apply said acceleration limit by modifying a response of said controller to said control signals, such that said motorised vehicle does not exceed said acceleration limit;
 wherein said motor arrangement drives at least a left wheel and a right wheel and said control signals comprise a demand speed and a demand spin,
 wherein said demand speed of said motorised vehicle is given by a mean of a demanded left wheel velocity and a demanded right wheel velocity,
 wherein said demand spin of said motorised vehicle is given by a mean difference of said demanded left wheel velocity and said demanded right wheel velocity, and
 wherein said acceleration control unit calculates said centripetal force factor in dependence on a product of said demand speed and said demand spin.

2. The controller as claimed in claim 1, wherein said acceleration control unit is configured to modify said response of said controller by limiting a rate of change of said demand speed.

3. The controller as claimed in claim 2, wherein said acceleration control unit is configured to limit said rate of change of said demand speed by applying a scaling factor to said rate of change, wherein said scaling factor is determined according to the formula: 1−(TTL*demand speed*demand spin), wherein TTL is a preprogrammed factor.

4. The controller as claimed in claim 1, wherein said acceleration control unit is configured to apply said acceleration limit only for increasing demand speed.

5. The controller as claimed in claim 1, wherein said demand speed and said demand spin are damped.

6. The controller as claimed in claim 1, wherein said acceleration control unit is configured to determine said centripetal force as a centripetal acceleration of said motorised vehicle.

7. The controller as claimed in claim 2, wherein said acceleration control unit is configured to effect said rate of change of said demand speed by applying a sequence of discrete increments to said demand speed.

8. The controller as claimed in claim 7, wherein said acceleration control unit is configured to apply said acceleration limit by reducing an increment size of said discrete increments.

9. The controller as claimed in claim 8, wherein said acceleration control unit is configured to provide a non-zero minimum increment size of said discrete increments.

10. The controller as claimed in claim 1, wherein said motorised vehicle is a front wheel drive vehicle.

11. The controller as claimed in claim 10, wherein said acceleration control unit is configured to apply said acceleration limit only for increasing demand speed, wherein said acceleration control unit is configured to apply said acceleration limit only for increasing demand speed in a forward direction.

12. The controller as claimed in claim 1, for use in a motorised vehicle taking the form of a wheelchair.

13. A motorised vehicle comprising:
 at least two wheels driven by a motor arrangement; and
 a controller for controlling the motor arrangement in dependence on said control signals, the controller comprising:
  a user-actuated input control module comprising a user actuated control element and an output, the input control module capable of providing control signals at said output; and
  a control unit having an input operably coupled to the output of the control module for receipt of the control signals, the control unit comprising:
   an acceleration control unit configured to determine, as a result of said control signals, a centripetal force factor corresponding to a centripetal force currently acting on said motorised vehicle and configured to calculate an acceleration limit for said motorised vehicle in dependence on said centripetal force factor,
   wherein said acceleration control unit is configured to apply said acceleration limit by modifying a response of said controller to said control signals, such that said motorised vehicle does not exceed said acceleration limit;

wherein said motor arrangement drives at least a left wheel and a right wheel and said control signals comprise a demand speed and a demand spin, wherein said demand speed of said motorised vehicle is given by a mean of a demanded left wheel velocity and a demanded right wheel velocity, wherein said demand spin of said motorised vehicle is given by a mean difference of said demanded left wheel velocity and said demanded right wheel velocity, and wherein said acceleration control unit calculates said centripetal force factor in dependence on a product of said demand speed and said demand spin.

14. The motorised vehicle as claimed in claim 13, wherein said motorised vehicle is a wheelchair.

15. A method of controlling a motorised vehicle having a motor arrangement, comprising the steps of:

receiving control signals from a user input device of the motorised vehicle and controlling said motor arrangement in dependence on said control signals;

determining, by a control unit, a centripetal force factor, corresponding to a centripetal force which is currently acting on said motorised vehicle, based upon said control signals;

calculating an acceleration limit for said motorised vehicle in dependence on said centripetal force factor;

modifying a response to said control signals based on said calculated acceleration limit; and the motorized vehicle limiting its acceleration to the calculated acceleration limit based upon said modified response;

wherein said motor arrangement drives at least a left wheel and a right wheel and said control signals comprise a demand speed and a demand spin, wherein said demand speed of said motorised vehicle is given by a mean of a demanded left wheel velocity and a demanded right wheel velocity, wherein said demand spin of said motorised vehicle is given by a mean difference of said demanded left wheel velocity and said demanded right wheel velocity, and wherein said acceleration control unit calculates said centripetal force factor in dependence on a product of said demand speed and said demand spin.

16. An article of manufacture, for use with a motorised vehicle having a motor arrangement, including computer program instructions stored on a non-transient storage medium that, when executed on a processor, cause the processor to perform actions comprising:

receiving control signals from a user input device of the motorised vehicle and controlling said motor arrangement in dependence on said control signals;

determining a centripetal force factor, corresponding to a centripetal force which is currently acting on said motorised vehicle, based upon said control signals;

calculating an acceleration limit for said motorised vehicle in dependence on said centripetal force factor; modifying a response to said control signals based upon said calculated acceleration limit; and the motorized vehicle limiting its acceleration to the calculated acceleration limit based upon said modified response;

wherein said motor arrangement drives at least a left wheel and a right wheel and said control signals comprise a demand speed and a demand spin, wherein said demand speed of said motorised vehicle is given by a mean of a demanded left wheel velocity and a demanded right wheel velocity, wherein said demand spin of said motorised vehicle is given by a mean difference of said demanded left wheel velocity and said demanded right wheel velocity, and wherein said acceleration control unit calculates said centripetal force factor in dependence on a product of said demand speed and said demand spin.

17. A controller for a motorised vehicle of a type having at least two wheels driven by a motor arrangement, the controller comprising:

a user-actuated input control means, comprising a user actuated control element and an output, for providing control signals at said output; and a control unit having an input operably coupled to the output of the input control means for receipt of the control signals, the control unit comprising:

an acceleration control means for determining, as a result of said control signals, a centripetal force factor corresponding to a centripetal force which is currently acting on said motorised vehicle and for calculating an acceleration limit for said motorised vehicle in dependence on said centripetal force factor; and said acceleration control means for applying said acceleration limit by modifying a response of said controller to said control signals, such that said motorized vehicle does not exceed said acceleration limit;

wherein said motor arrangement drives at least a left wheel and a right wheel and said control signals comprise a demand speed and a demand spin, wherein said demand speed of said motorised vehicle is given by a mean of a demanded left wheel velocity and a demanded right wheel velocity, wherein said demand spin of said motorised vehicle is given by a mean difference of said demanded left wheel velocity and said demanded right wheel velocity, and wherein said acceleration control unit calculates said centripetal force factor in dependence on a product of said demand speed and said demand spin.

* * * * *